United States Patent
Naish

(10) Patent No.: US 11,284,608 B2
(45) Date of Patent: Mar. 29, 2022

(54) AQUACULTURE SYSTEM AND METHOD

(71) Applicant: Oxitec Limited, Abingdon (GB)

(72) Inventor: Neil Naish, Abingdon (GB)

(73) Assignee: Oxitec Limited, Abingdon (GB)

( * ) Notice: Subject to any disclaimer, the term of this patent is extended or adjusted under 35 U.S.C. 154(b) by 348 days.

(21) Appl. No.: 15/503,352

(22) PCT Filed: Aug. 11, 2015

(86) PCT No.: PCT/IB2015/001823
§ 371 (c)(1),
(2) Date: Feb. 10, 2017

(87) PCT Pub. No.: WO2016/024164
PCT Pub. Date: Feb. 18, 2016

(65) Prior Publication Data
US 2018/0213756 A1    Aug. 2, 2018

(30) Foreign Application Priority Data
Aug. 11, 2014    (GB) .................................... 1414210

(51) Int. Cl.
*A01K 67/033*    (2006.01)
(52) U.S. Cl.
CPC .................. *A01K 67/033* (2013.01)
(58) Field of Classification Search
CPC ........................ A01K 67/033; A01K 67/0339
See application file for complete search history.

(56) References Cited

U.S. PATENT DOCUMENTS

| | | | |
|---|---|---|---|
| 742,158 A | 10/1903 | Burke | |
| 1,289,778 A | 12/1918 | Houck | |
| 3,082,138 A | 3/1963 | Day et al. | |
| 3,204,605 A | 9/1965 | Vroman | |
| 3,223,237 A * | 12/1965 | Harrod, Jr. ........... | A01K 67/033 209/2 |
| 3,661,119 A | 5/1972 | Sanders | |
| 3,682,138 A | 8/1972 | Day et al. | |
| 3,696,788 A | 10/1972 | Day et al. | |

(Continued)

FOREIGN PATENT DOCUMENTS

| | | |
|---|---|---|
| CN | 201374958 | 1/2010 |
| GB | 408 050 | 4/1934 |

(Continued)

OTHER PUBLICATIONS

Ansari et al., "A device for separation of pupae from larvae of Aedes aegypti (Diptera: Culicidae)," J. Med. Entomol. (1977) 14(2):241-243.

(Continued)

*Primary Examiner* — Christopher D Hutchens
(74) *Attorney, Agent, or Firm* — Morrison & Foerster LLP

(57) ABSTRACT

In one aspect, provided herein is an apparatus for mass rearing aquatic arthropod larvae that provides control over the environment in which the larvae are reared. The apparatus comprises an aquatic reservoir, means to supply water to the reservoir, and means to drain water from the reservoir, said drainage means being equipped with a porous barrier, such as a sieve, adapted to prevent said larvae from exiting the reservoir therethrough, while permitting the passage of water.

26 Claims, 3 Drawing Sheets

(56) References Cited

U.S. PATENT DOCUMENTS

| | | | |
|---|---|---|---|
| 3,833,119 A | | 9/1974 | Brown |
| 3,861,119 A | | 1/1975 | Taggart |
| 5,133,289 A | * | 7/1992 | Georgi .................. A01K 67/033 119/6.6 |
| 5,248,046 A | | 9/1993 | Rollason |
| 5,759,224 A | * | 6/1998 | Olivier .................. A01K 67/033 435/290.4 |
| 5,873,327 A | | 2/1999 | Holyoak |
| 6,474,259 B1 | * | 11/2002 | Gaugler ............... A01K 67/033 119/6.7 |
| 6,990,768 B1 | * | 1/2006 | Boston .................... A01M 1/02 119/69.5 |
| 7,134,238 B2 | | 11/2006 | Forehand |
| 7,448,498 B2 | | 11/2008 | McRobert |
| 8,844,465 B2 | | 9/2014 | Holland et al. |
| 10,159,228 B2 | * | 12/2018 | Hall ...................... A01K 67/033 |
| 10,342,222 B2 | * | 7/2019 | Sobecki .................. B07B 1/469 |
| 2006/0248782 A1 | * | 11/2006 | Dancy ................... A01M 1/106 43/107 |
| 2012/0017834 A1 | | 1/2012 | Holland et al. |
| 2013/0168327 A1 | * | 7/2013 | Clark .................... G01N 31/22 210/739 |
| 2013/0319334 A1 | * | 12/2013 | Newton ............... A01K 67/033 119/6.5 |
| 2014/0332448 A1 | | 11/2014 | Trivette et al. |
| 2015/0296759 A1 | | 10/2015 | Guichou et al. |
| 2019/0191677 A1 | * | 6/2019 | Massaro ............... A01K 67/033 |

FOREIGN PATENT DOCUMENTS

| | | |
|---|---|---|
| JP | 2009/178139 | 8/2009 |
| WO | WO-01/39599 | 6/2001 |
| WO | WO-2013/190142 | 12/2013 |

OTHER PUBLICATIONS

Ansari et al., The development of procedures formass rearing of Aedes aegypti (I). WHO/VBC/75.560:9P (1975) 9 pages.

Ansari et al., "The development of procedures and techniques for mass rearing of Aedes aegypti," Indian J. Med. Res (1977) 65(Suppl):91-99.

Balestrino et al., "A New Larval Tray and Rack System for Improved Mosquito Mass Rearing," J Med Entomol (2012) 49(3):595-605.

Dame et al., "Release of chemosterilized males for the control of Anopheles albimanus in El Salvador. II Methods of rearing, sterilizations and distribution," Am J Trap Med and Hyg (1974) 22(2):282-287.

Evans et al., "A simple separator for mosquito larvae and pupae," Mosq. News (1968) 28(4):649-650.

Fay et al., "A mechanical device for separating the developmental stages, sexes, and species of mosquitos," Mosq. News (1959) 19:144-147.

Fay et al., "Mass production of sterilized male Aedes aegypti," (1963) Mosq. News 23(3):210-214.

Focks, "An improved separator for the developmental stages, sexes, and species of mosquitoes (Diptera: Culicidae)," J. Med. Entomol. (1980) 17:567-568.

Gerberg et al., "Mass rearing of Culex pipiens," Mosquito News (1969) 29(3):382-385.

Hazard, "Modification of the ice water method for harvesting Anopheles and Culex pupae," Mosq. News (1967) 27:115-116.

International Search Report and Written Opinion for PCT/IB2015/001823, dated Dec. 18, 2015, 8 pages.

Lin et al., "Tolerance of mosquito larvae and pupae to carbon dioxide anesthesia," Mosq. News (1976) 36:460-461.

McCray, "A mechanical device for the rapid sexing of Aedes aegypti pupae," J. Econ. Entomol. (1961) 54:819.

Morlan et al., "Methods for mass rearing of Aedes aegypti (L.)," Public Health Rep (1963) 78(8):711-720.

Ramakrishnan et al., "A simple technique for rapid separation of mosquito pupae by sudden chilling," (1963) Indian J. Malarlol. (1963) 17(2/3):119-121.

Sharma et al., Bulletin of WHO, p. 429-432, 1974.

Singh et al., "Mass rearing of Culex fatigans," WHO/VBC/72.386 (1972).

Singh et al., "Mass rearing of Culex pipiens fatigans WIED," J. Com. Dis (1975) 7(1):31-53.

Weathersby, "Harvesting mosquito pupae with cold water," Mosq. News (1963) 23(3):249-251.

* cited by examiner

AQUACULTURE SYSTEM AND METHOD

CROSS REFERENCE TO RELATED APPLICATIONS

This application is a U.S. National Phase of International Application No. PCT/IB2015/001823, filed Aug. 11, 2015, which claims the benefit of priority of GB Patent Application No. 1414210.3, filed Aug. 11, 2014, the contents of which are incorporated herein by reference in their entireties.

FIELD OF THE INVENTION

The present disclosure in some aspects relates to apparatus and methods for rearing aquatic arthropod larvae. In particular aspects, the present disclosure relates to mass rearing of insect larvae, especially pest insect, for use in biological control.

BACKGROUND OF THE INVENTION

Insect pests can cause damaging infestations of crops or transmit diseases. The expanding population of such insect pests may be countered using biological control. One example of biological control is sterile insect technique (SIT), a species-specific and environmentally non-polluting system for management of key insect pests of agricultural or medical importance. The system involves mass rearing millions of insects and sterilizing the males by exposing them to low doses of radiation. The sterile males are released into the environment, wherein they compete with the wild males for mates. Females which mate with sterile males produce no offspring, and the sequential release of large numbers of sterile males, therefore, leads to a decrease in the population size of the next generation. In this way the size of the wild population is controlled.

A transgenic alternative to radiation-sterilization, termed Self-Limiting System, is also available. In this system, insects are engineered to carry a gene that is self-limiting and, in the absence of antidote, insects carrying this gene fail to mature to functional adults capable of mating and flight. The expression of the self-limiting gene may be repressible, for example by using a Tet-Off system. These insects are released into the wild where progeny, resulting from mating between wild insects and self-limiting insects that inherit a copy of the self-limiting gene or construct, will tend to die. The Self-Limiting system may be designed to kill all progeny that inherit it, or only one sex. It may also be designed to kill the affected insects at a particular stage in development; this may have significant advantages in some species, e.g., some mosquitoes. Self-Limiting systems have been constructed in a number of pest species. Further information on the Self-Limiting system may be found in WO 01/39599.

Biological control methods require mass rearing of organisms for release into the wild. In order for biological control to be successful, the continuous production of large numbers of high quality insects is essential.

SUMMARY

The summary is not intended to be used to limit the scope of the claimed subject matter. Other features, details, utilities, and advantages of the claimed subject matter will be apparent from the detailed description including those aspects disclosed in the accompanying drawings and in the appended claims.

In one aspect, disclosed herein is an apparatus for mass rearing aquatic arthropod larvae, comprising an aquatic reservoir, means to supply water to the reservoir, and means to drain water from the reservoir, said drainage means being equipped with a porous barrier, such as a sieve, adapted to prevent said larvae from exiting the reservoir therethrough, while permitting the passage of water.

In one embodiment, the means to supply water to the reservoir is arranged to recycle the water drained from the reservoir.

In any of the preceding embodiments, the means to supply water to the reservoir can comprise a filter. In one aspect, the filter is one or more of the following: a mechanical filter, a biological filter and a chemical filter, or a combination thereof.

In any of the preceding embodiments, the means to supply water to the reservoir can comprise a water tank for storing water supplied to the reservoir.

In any of the preceding embodiments, the apparatus can further comprise a sensor for measuring a specific property of the water supplied to the reservoir.

In any of the preceding embodiments, the apparatus can further comprise a means for automating the apparatus. In one aspect, the means for automating the apparatus is a microcontroller.

In any of the preceding embodiments, the means to drain water from the reservoir can be removable from the reservoir.

In any of the preceding embodiments, the reservoir can further comprise a levelling valve arranged to maintain a minimum level of water in the reservoir.

In any of the preceding embodiments, the aquatic reservoir can comprise an overflow valve. In one aspect, the overflow valve is positioned 180° on the horizontal plane to the position where the water enters the aquatic reservoir.

In another aspect, provided herein is a method of mass rearing aquatic arthropod larvae, comprising equipping an aquatic reservoir with a porous barrier, said reservoir having means to supply water thereto and means to drain water therefrom, placing aquatic arthropod larvae within said reservoir, said barrier being adapted to prevent escape of the larvae while permitting passage of water and replacing the water in the reservoir on a continual basis while rearing the larvae.

In any of the preceding embodiments, the arthropod larvae can be placed within the reservoir such that the surface area density of larvae within the reservoir is 10 per square centimeter. In any of the preceding embodiments, replacement of the water can be automated.

In any of the preceding embodiments, the method can further comprise a step of adjusting the property of the water to be supplied to optimal conditions for rearing aquatic arthropod larvae prior to replacement of the water in the reservoir.

In any of the preceding embodiments, the property of water to be adjusted can be one or more of the following: concentration of oxygen, temperature, pH, conductivity, ORP and concentration of a chemical compound.

In any of the preceding embodiments, the step of adjusting the property of the water to be supplied can be automated.

In one aspect, provided herein is an apparatus for rearing aquatic arthropod larvae. In some embodiments, the apparatus comprises a container comprising a porous barrier which partitions the container into a first chamber and a second chamber. In one aspect, the second chamber comprises a drain outlet. In another aspect, the porous barrier is capable of preventing the larvae from exiting the first chamber into the second chamber while permitting at least the passage of water between the chambers, when water is supplied to the first chamber and drained from the container via the drain outlet of the second chamber.

In some embodiments, the drain outlet comprises a valve and/or a pipe sealed or affixed on the drain outlet opening. In one aspect, the valve is an overflow valve, and water passes from the container through the overflow valve after the maximum water level has been attained in the container.

In any of the preceding embodiments, the drain outlet can be positioned substantially 180° on a horizontal plane to the position where water enters the container. In any of the preceding embodiments, the apparatus can further comprise a pipe for supplying water to the container. In one embodiment, the pipe for supplying water comprises a filter. In another embodiment, the filter is a mechanical filter, a biological filter, a chemical filter, or a combination thereof.

In any of the preceding embodiments, the apparatus can further comprise a water tank connected, directly or indirectly, to the pipe for supplying water to the container, and the water tank stores water supplied to the container. In one aspect, the water tank is connected, directly or indirectly, to the drain outlet of the second chamber, and water drained from the container is recycled and supplied to the container. In another aspect, the water tank is connected to the drain outlet via a filtering device capable of filtering water drained from the container. In yet another aspect, the filtering device comprises a filter and a waste outlet for removing waste.

In any of the preceding embodiments, the apparatus can further comprise a sensor for measuring a property of water supplied to and/or drained from the container. In some aspects, the property of water is concentration of oxygen, temperature, pH, conductivity, oxidation-reduction potential (ORP), or concentration of a chemical compound.

In any of the preceding embodiments, the apparatus can further comprise a levelling valve arranged to maintain a minimum level of water in the container. In any of the preceding embodiments, the apparatus can further comprise a microcontroller for automating the apparatus.

In any of the preceding embodiments, the porous barrier can be removable from the container. In any of the preceding embodiments, the porous barrier can have an average aperture diameter ranging from about 100 µm to about 1,000 µm, or from about 123 µm to about 152 µm. In any of the preceding embodiments, the porous barrier can comprise mesh holes that are round, square, rectangular, elliptical, oval, or of any other suitable shape. In any of the preceding embodiments, the porous barrier can permit the passage of feed, waste, and other debris, including waste produced by the larvae. In any of the preceding embodiments, the porous barrier can comprise a mesh, membrane, screen, paper, woven cloth, non-woven cloth, fabric, fiber, foam, sieve, entangled wires, electrospun polymeric fiber, or a combination thereof. In some embodiments, the porous barrier can have an average wire diameter ranging from about 1 µm to about 1,000 µm.

In any of the preceding embodiments, the apparatus can be used for mass rearing of the aquatic arthropod larvae. In any of the preceding embodiments, the apparatus can be used for rearing aquatic arthropod larvae at a density ranging from about one larva to about 12 larvae per cm2 of the bottom plate of the container, or at a density of about 10 larvae per cm2 of the bottom plate of the container. In any of the preceding embodiments, the apparatus can be used for rearing aquatic arthropod larvae at a density ranging from about 1,500 larvae to about 4,000 larvae per liter of water in the container.

In any of the preceding embodiments, the apparatus can comprise a plurality of the containers. In some embodiments, the apparatus comprises about 5, 10, 100, 500, 1,000, 5,000, or more of the containers. In some embodiments, at least some of the containers are sequentially connected to each other or stacked on top of one another. Water passes from the first container in the sequence or stack through intervening container(s) to the last container in the sequence or stack. The first container is connected to or supplied by (e.g., not physically connected to) a pipe supplying water and the last container is connected to a pipe draining water, and the drained water is recycled to the first container. In other embodiments, at least some of the containers are connected in parallel to the pipe supplying water and/or the pipe draining water, and the drained water is recycled to the containers.

In another aspect, disclosed herein is an apparatus for rearing aquatic arthropod larvae, comprising a first container and a second container constructed substantially similar to the first container. In some embodiments, the first container comprises a porous barrier which partitions the first container into a first chamber and a second chamber, and the second chamber comprises a drain outlet. In one aspect, the porous barrier is capable of preventing the larvae from exiting the first chamber into the second chamber while permitting at least the passage of water between the chambers, when water is supplied to the first chamber and drained from the first container via the drain outlet of the second chamber. In another aspect, water drained from the first container passes into the first chamber of the second container. In yet another aspect, the apparatus further comprises a rack on which the first and second containers are disposed.

In any of the preceding embodiments, the first container can be vertically stacked above the second container. In any of the preceding embodiments, the drain outlet of the first and/or container can comprise a valve and/or a pipe sealed or affixed on the drain outlet opening. In one aspect, the valve is an overflow valve, and water passes from the first container through the overflow valve after the maximum water level has been attained in the first container into the second container.

In any of the preceding embodiments, the drain outlet of each container can be positioned substantially 180° on a horizontal plane to the position where water enters the container. In any of the preceding embodiments, the apparatus can further comprise a pipe for supplying water to the first container. In one aspect, the pipe for supplying water comprises a filter, for example, a mechanical filter, a biological filter, a chemical filter, or a combination thereof.

In any of the preceding embodiments, the apparatus can further comprise a water tank connected, directly or indirectly, to the pipe for supplying water to the first container, and the water tank stores water supplied to the containers. In one aspect, the water tank is connected, directly or indirectly, to the drain outlet of the second container, and water drained from the second container is recycled and supplied to the first container. In another aspect, the water tank is connected to the drain outlet via a filtering device capable of filtering water drained from the second container. In yet another aspect, the filtering device comprises a filter and a waste outlet for removing waste.

In any of the preceding embodiments, the apparatus can further comprise a sensor for measuring a property of water supplied to and/or drained from the containers. In one aspect, the property of water is concentration of oxygen, temperature, pH, conductivity, oxidation-reduction potential (ORP), or concentration of a chemical compound.

In any of the preceding embodiments, each container can comprise a levelling valve arranged to maintain a minimum level of water in the container. In any of the preceding embodiments, the apparatus can further comprise a microcontroller for automating the apparatus.

In any of the preceding embodiments, the porous barrier can be removable from each container. In any of the preceding embodiments, the porous barrier in each container can have an average aperture diameter ranging from about 100 μm to about 1,000 μm, or from about 123 μm to about 152 μm. In any of the preceding embodiments, the porous barrier can permit the passage of feed, waste, and other debris, including waste produced by the larvae. In any of the preceding embodiments, the porous barrier in each container can comprise a mesh, membrane, screen, paper, woven cloth, non-woven cloth, fabric, fiber, foam, sieve, entangled wires, electrospun polymeric fiber, or a combination thereof. In some aspects, the porous barrier in each container has an average wire diameter ranging from about 1 μm to about 1,000 μm.

In any of the preceding embodiments, the apparatus can be used for mass rearing of the aquatic arthropod larvae. In any of the preceding embodiments, the apparatus can be used for rearing aquatic arthropod larvae at a density ranging from about one larva to about 12 larvae per cm2 of the bottom plate of each container, or at a density of about 10 larvae per cm2 of the bottom plate of the container. In any of the preceding embodiments, the apparatus can be used for rearing aquatic arthropod larvae at a density ranging from about 1,500 larvae to about 4,000 larvae per liter of water in each container.

In another aspect, disclosed herein is a method for rearing aquatic arthropod larvae, comprising: (1) placing larvae or eggs of an aquatic arthropod in a first chamber of a container; the container comprises a porous barrier that separates the first chamber from a second chamber of the container; the second chamber comprise a drain outlet, and the porous barrier is capable of preventing the larvae from exiting the first chamber into the second chamber while permitting at least the passage of water between the chambers; and (2) supplying water on a continual basis and other suitable conditions in the container for rearing the larvae or eggs in the first chamber, and water is drained from the container via the drain outlet of the second chamber. In one aspect, the drain outlet comprises a valve and/or a pipe sealed or affixed on the drain outlet opening. In another aspect, the valve is an overflow valve, and water passes from the container through the overflow valve after the maximum water level has been attained in the container.

In any of the preceding embodiments, the drain outlet can be positioned substantially 180° on a horizontal plane to the position where water enters the container. In any of the preceding embodiments, the method can further comprise filtering the water before it is supplied to the container. In any of the preceding embodiments, water can be supplied to the container by a pipe connected to a water tank. In one aspect, the water tank is connected, directly or indirectly, to the drain outlet of the second chamber, and the method further comprises recycling water drained from the container.

In any of the preceding embodiments, the method can further comprise filtering water drained from the container. In any of the preceding embodiments, the method can further comprise removing waste from water drained from the container. In any of the preceding embodiments, the method can further comprise measuring a property of water supplied to and/or drained from the container. In any of the preceding embodiments, the method can further comprise adjusting a property of the water drained from the container and/or to be supplied to the container, to optimal conditions for rearing aquatic arthropod larvae. In one aspect, the property of water is concentration of oxygen, temperature, pH, conductivity, oxidation-reduction potential (ORP), or concentration of a chemical compound.

In any of the preceding embodiments, the method can further comprise maintaining a minimum level of water in the container.

In any of the preceding embodiments, the porous barrier can be removable from the container. In any of the preceding embodiments, the porous barrier can have an average aperture diameter ranging from about 100 μm to about 1,000 μm, or from about 123 μm to about 152 μm. In any of the preceding embodiments, the porous barrier can permit the passage of feed, waste, and other debris, including waste produced by the larvae. In any of the preceding embodiments, the porous barrier can comprise a mesh, membrane, screen, paper, woven cloth, non-woven cloth, fabric, fiber, foam, sieve, entangled wires, electrospun polymeric fiber, or a combination thereof. In one aspect, the porous barrier has an average wire diameter ranging from about 1 μm to about 1,000 μm.

In any of the preceding embodiments, the method can be used for mass rearing of the aquatic arthropod larvae. In any of the preceding embodiments, the method can be used for rearing aquatic arthropod larvae at a density ranging from about one larva to about 12 larvae per cm2 of the bottom plate of the container, or at a density of about 10 larvae per cm2 of the bottom plate of the container. In any of the preceding embodiments, the method can be used for rearing aquatic arthropod larvae at a density ranging from about 1,500 larvae to about 4,000 larvae per liter of water in the container.

In some embodiments, water is supplied to the container at a flow rate of between about 0.5 L/min and about 5 L/min, or at about 3 L/min. In any of the preceding embodiments, the flow rate of water draining from the container can be substantially the same as the flow rate at which water is supplied to the container. In any of the preceding embodiments, the method can further comprise adjusting the flow rate at which water is supplied to the container. In any of the preceding embodiments, the method can further comprise adjusting the flow rate of water draining from the container.

In any of the preceding embodiments, water can be supplied to the container at a flow rate that maintains the temperature in the container at about 22±3° C., about 26±2° C., or between about 25° C. and 28° C. A suitable temperature range for rearing an aquatic arthropod is known to one of skill in the art and/or can be determined.

In any of the preceding embodiments, the method can use a plurality of the containers comprising a porous barrier. In one aspect, about 5, 10, 100, 500, 1,000, 5,000, or more of the containers are used. In some embodiments, at least some of the plurality of containers are sequentially connected to each other or stacked on top of one another. Water passes from the first container in the sequence or stack through intervening container(s) to the last container in the sequence or stack. The first container is connected to or supplied by (e.g., not physically connected to) a pipe supplying water and the last container is connected to a pipe draining water, and the drained water is recycled to the first container. In some embodiments, at least some of the containers are connected in parallel to the pipe supplying water and/or the pipe draining water, and the drained water is recycled to the containers.

In any of the preceding embodiments, water can be supplied to each container at a flow rate of between about 0.5 L/min and about 5 L/min, or at about 3 L/min. In any of the preceding embodiments, the flow rate at which water is supplied to each container can be substantially the same as the flow rate at which water is supplied to the next connected or stacked container. In any of the preceding embodiments, water can be supplied to the each container at a flow rate that maintains the temperature in the containers at about 22±3° C., about 26±2° C., or between about 25° C. and 28° C.

In any of the preceding embodiments, at least one of steps can be automated.

In any of the preceding embodiments, the aquatic arthropod can be a pest. In any of the preceding embodiments, the aquatic arthropod can be an insect. In one embodiment, the insect is a mosquito. In some embodiments, the mosquito is from the genera *Stegomyia, Aedes, Anopheles, Culex,* or *Toxorhynchites*. In some embodiments, the mosquito is selected from *Aedes aegypti, Aedes albopictus, Culex pipiens, Culex quinqufaciatis, Anopheles stephensi, Anopheles albimanus,* and *Anopheles gambiae*.

DETAILED DESCRIPTION

Figure 1:
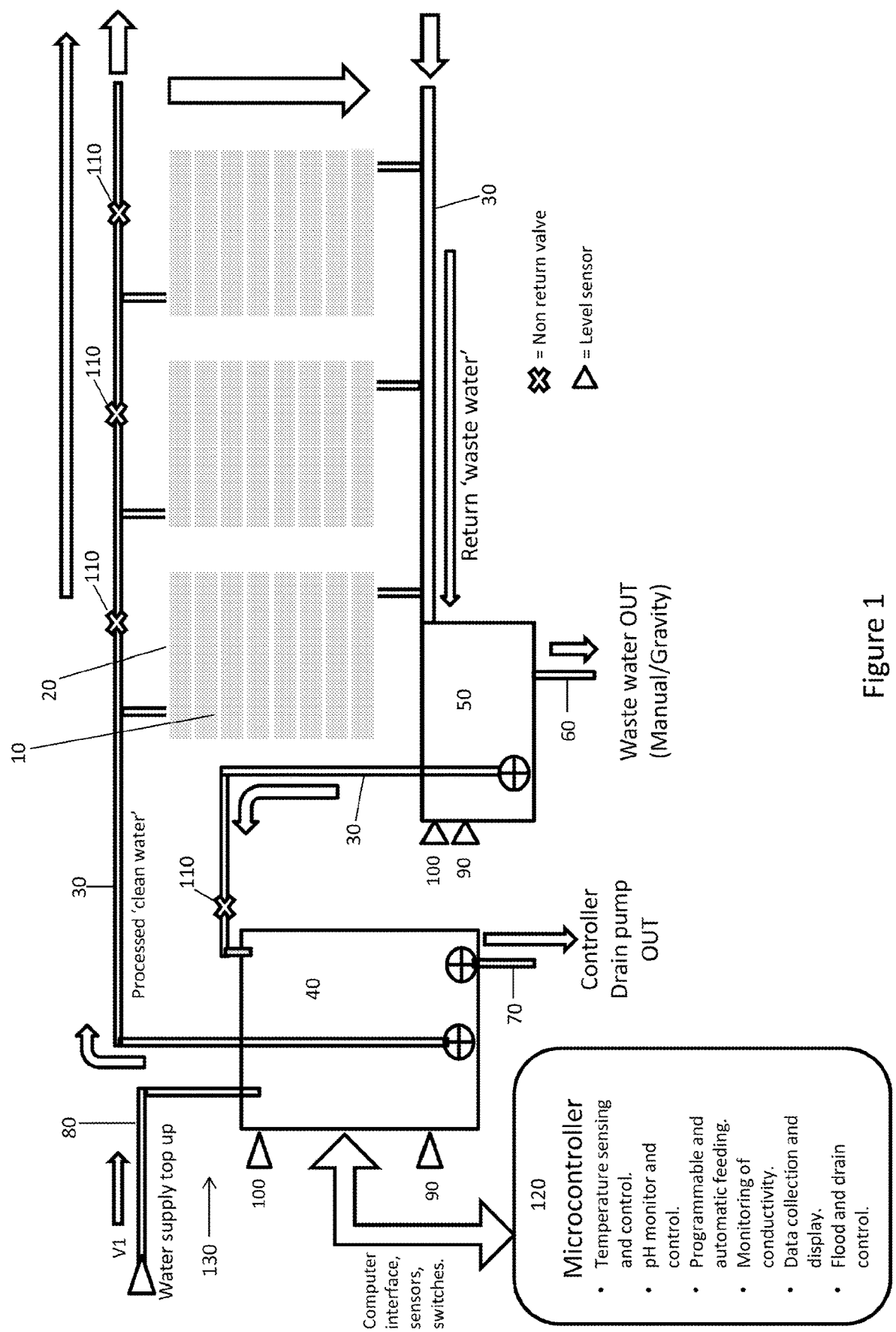
FIG. 1 shows a schematic representation of an apparatus according to an embodiment of the present disclosure.

Provided herein are apparatus and methods utilizing a cascading system of trays where water moves between layers on a re-circulating basis and is also retained in layers for rearing aquatic arthropod larvae. In one aspect, the apparatus disclosed herein comprises a sieve structure which reduces water flow rate sufficiently to ensure that the constant flow of water at a flow rate that does not force the vulnerable larvae to be trapped at the drain point and die, or for the sieve structure to overflow (which also results in death). In some embodiments, provided herein is an apparatus that prevents scum formation, water spoilage, temperature stratification and evaporation of water from the shallow trays, for mass rearing aquatic arthropod larvae.

The larval stage of all mosquitoes is aquatic and requires specific conditions in which to thrive, particularly under intensive mass production conditions. The larvae are subject to stress due to over-crowding, poor water quality and abnormal rearing environment to name just a few. Procedures and techniques for mass rearing of mosquito larvae typically employ the use of multiple shelves or layers of trays each containing a specified volume of water, a controlled amount of food and a specified number of larvae in each tray.

Morlan et al. (1963) detailed their methods for rearing up to 1.3 million *Ae. aegypti* larvae per brood, of which 0.5 to 0.8 million adults were produced within 11 days. This was achieved using 192 trays (183 cm×26 cm×5 cm) supported in eight metal racks, each containing 24 rearing trays. Each tray held 7 liters of water and 7000 larvae resulting in a larval density of 1 larva per mL and surface area density of 1.4 larvae per $cm^2$. Morlan et al. considered greater capacity could be possible with additional rearing equipment and personnel against the two men originally employed.

Fay et al. (1963) reported in the same year that they also had reared *Ae. aegypti* in the same sized trays as Morlan et al. but with a larger number of insects per tray. This production was carried out using a system comprising 13 racks containing 12 trays per rack with each tray containing 8000 larvae in 8 liters of water. This resulted in a maximum production capacity of approximately 1.25 million pupae when all trays were used at once. Their studies did highlight that increased capacity might be possible by modifying the larval density within their tray. Increasing from 8,000 to 15,000 larvae per tray resulted in no apparent change in survival or insect quality but this scale up process was not pursued.

It is also reported that Gerberg et al. (1969) in the Insect Control and Research (ICR) laboratories, Baltimore, USA were able to rear *Culex pipiens* in large trays (137.6 cm×76.2 cm×5.08 cm), each containing 10,000 larvae. The resulting surface area density was slightly under 1 larva per $cm^2$ and volume density of 2.65 larvae per mL.

Ansari et al. (1977) reported a production of 250,000 to 400,000 pupae per day using large trays (60 cm×63 cm×9 cm) each containing 30,000 larvae per tray in 22 liters of water and in stacks of 13 tray units. This represents a change from the more conservative rearing conditions described earlier to a more intensive surface area density of 7.9 larvae per $cm^2$. However, Ansari et al. reported issues with scum formation, water spoilage, difficulties with water level control and problematic food delivery to the multi-tray system. Drainage tubes were fitted to each tray to enable rapid emptying but no automation or attempts to resolve the problems were pursued. These rearing methods had also been previously used for the mass production of *Culex pipiens* with similar success (Singh et al. 1975, 1977). In this production system, some control over re-filling trays, agitating trays to prevent scum formation and draining the system was achieved. However, these controls were not aimed at forming an integrated system related to controlling the environmental rearing conditions, rather it served to improve the efficiency of the production process. The rearing method, surface area density and volume density were as previously described (Ansari et al. 1977).

More recently, Balestrino et al. (2012) at the International Atomic Energy Agency (IAEA) published a stacked tray system for improved mass rearing of mosquito larvae. As part of a program to develop suitable equipment for use in the SIT control of *Anopheles arabiensis*, a tray stacking unit consisting of 50 ABS (acrilonitile butadiene styrene) plastic trays was reported to be able to support development of up to 175,000 adults or 4,000 larvae per tray of that species. The dimensions of the trays are 100 cm×60 cm×3 cm and are incorporated into a pouring stack system where all of the trays can be simultaneously tilted and their contents poured into a retrieval system for post processing. This is a manual process. The production of Anopheline mosquitoes by Dame et al. (1974) results in their rearing at a shallow water depth (<2 cm). However, in both of these examples for Anopheline mosquitoes, and in examples for different mosquito species, although shallow trays or shallow rearing depths are often quoted in descriptions, the water depth often results from the choice of container and does not reflect an active decision as a specific or optimized rearing improvement.

The publication by Balestrino et al. (2012) also states the system has been used to demonstrate some larval rearing with *Ae. albopictus* but not to any significant scale. Further communications indicate that the system has been used to rear 12,000 *Ae. albopictus* larvae per tray in a few of its 50 trays, however, again this is not at full capacity rather it is in order to test its potential. If it was used at full capacity it is quoted as being about to hold 600,000 larvae in a footprint of approximately 0.6 m×1.0 m and a total height of 2.0 m. Even at the scale it has been tested at, problems were reported with temperature variations within the tray stack levels. Temperature stability is essential to enable uniform development time of the insects and to ensure equal size and synchronicity of cohorts in both lab and particularly field applications. This system also used a defined diet that prevented scum formation that can cause problems with rearing if left unattended, which partially addresses some of the reasons behind tray spoilage without investigating or controlling water chemistry directly. Evaporation from large shallow trays was also noted as being an issue. The trays are able to self-fill from above due to an internal overflow vent system but this is not part of the rearing system per se.

Holyoak (U.S. Pat. No. 5,873,327) describes a system and method for cultivating amphibians (frogs) in captivity. The Holyoak device consists of multiple trays stacked above one another and a continuous water supply that circulates around the system arriving at a top tray and draining to a sump tank via a series of trays and standpipes that retain water to a specific height in each. Frogs are located within trays and are supplied with water on a continuous basis. Holyoak claims that this enables maximum production but there is no specific number of animals per tray or unit provided in the text.

Li (CN201374958Y) also describes a system for rearing three stripped box turtles. The description is similar to Holyoak above where a series of trays is fed with a continuous water supply and where the liquid drains through a filtered pipe into a tray beneath. Although suitability is claimed for rearing mass density of tortoises and other species breed, there is no stated figure for density or flow rate in the text. In addition, the primary role of the filter on the drain pipe is apparently to prevent feces in the upper tray from passing into the tray below.

Holyoak includes a fitted strainer on the standpipe as part of the system. This strainer is fitted to ensure that frogs do not move between tray layers. Although frogs are able to move away from the direction of water flow, they are physically able to hide and climb between layers. If large numbers (e.g., >25000) of 1st instar mosquito larvae (typically <1.4 mm long) are placed into a large rearing tray with a standpipe fitted and that the standpipe is covered with a filtering membrane that is of sufficient gauge to prevent larvae passing through either at the top or bottom of tube, then larvae are rapidly drawn to the drain point. Due to the continuous current created by the recirculating nature of the water system and the fragility of the L1 larvae, these larvae remain trapped against the mesh filter surface on the standpipe and die. See infra Example 1. The build-up of material on the sieve surface then increases as more larvae are drawn to the drain point which eventually leads to an over flow from the tray once the flow through the drain has been completely blocked. This overflow will also eventually results in larval death if allowed to occur.

Thus, there has been little advancement regarding the apparatus used in rearing mosquito larvae over the last 50 years. The prior devices and methods do not offer a solution to the mass production of mosquito larvae from egg to pupa.

As an illustration, a SIT program controlling yellow fever mosquito, *Aedes aegypti*, for a population of 10,000 people in an area requiring a practical release rate of 200 per head would need a production of approaching 2,000,000 male pupae per week.

As noted above, transgenic alternatives to SIT, such as the Self-Limiting system, require that the mosquitoes are reared under conditions in which the expression of the dominant lethal gene is repressed. This may, for example, be through the Tet-Off system in the presence of the antibiotic tetracycline and/or chemical analogues. In such cases, it is essential to the successful rearing of the mosquitos that tetracycline and/or chemical analogues are provided at the correct dose and at the correct stage of development of the mosquitoes.

In some embodiments, provided herein are apparatus and method utilizing a cascading system of trays where water moves between layers on a re-circulating basis and is also retained in layers by the use of simple open standpipes. In one aspect, the apparatus disclosed herein comprises a large sieve structure which reduces water flow rate sufficiently to ensure that the constant flow of water at the required flow rate does not force the vulnerable 1st instar larvae to a point that ultimately causes them to die or for the sieve structure to overflow (which also results in death). In addition to the large sieve structure, an open free running drain point is essential that will ensure free movement of water, waste and food between layers. In some embodiments, mosquito larvae are reared in large volumes of water at high density, and the apparatus disclosed herein has a specific flow rate and mesh size in order for the mass production to be successful. In some embodiments, optimum pupal production from a fixed area and water volume is provided using flow rate and mesh sizes that ensure success. In other embodiments, the apparatus comprises a sieve unit that sits in the rearing tray/water containing all of the larvae in production, and the sieve unit and/or tray is removable. For example, the sieve unit can be removed from the water in the rearing tray enabling all essential processing steps to be easily achieved. The sieve and aquaculture system therefore perform both a biological function in ensuring proper flow rate and optimum rearing conditions as well as a physical processing role essential to the mass production requirements of the equipment.

Therefore, in some embodiments, provided herein is an improved apparatus that prevents scum formation, water spoilage, temperature stratification and evaporation of water from the shallow trays, for mass rearing aquatic arthropod larvae. In some embodiments, provided herein is an improved apparatus that allows accurate control over the water level and food delivery to the trays.

In some embodiments, provided herein is an improved apparatus for mass rearing of aquatic arthropod larvae, which allows the distribution of specific chemical compounds, where required, at the correct dose.

Furthermore, with the increased need for biological control programs, scaling up of rearing programs from the laboratory to factory level production is desirable. The management of such a large operation represents considerable challenges and whilst there is the scalable option of increasing the number of personnel and equipment, large scale operations demand a need to improve rearing efficiency particularly when resources and funds are restricted. The need to reduce cost is closely related to the need to reduce factory space, number of personnel and process time. In some embodiments, provided herein is an automated apparatus designed to optimize rearing efficiency.

In some embodiments, the apparatus provided herein efficiently prevents and/or overcomes the problems associated with the current technology available for mass rearing aquatic arthropod larvae, and especially mosquito larvae.

Surprisingly, the inventor has found that it is possible to replace/recycle the water in the trays such as to overcome many or all of the problems associated with the current technology, despite some aquatic arthropod larvae having a preference for static water. Furthermore, it has also surprisingly now been found that surface area density (larvae per $cm^2$) is a limiting factor in survival of the larvae to pupation independently of effective volume densities (larvae per mL).

Thus, in one aspect, the present disclosure provides an apparatus for mass rearing aquatic arthropod larvae comprising an aquatic reservoir, means to supply water to the reservoir, and means to drain water from the reservoir. The drainage means is equipped with a porous barrier, such as a sieve, adapted to prevent the larvae from exiting the reservoir therethrough, while permitting the passage of water.

The term "aquatic arthropod" as used herein, refers to any arthropod with a life cycle comprising an aquatic life stage.

The apparatus of the present disclosure is particularly suited for mass rearing aquatic arthropod larvae, particularly insect larvae and even more suited for mass rearing mosquito larvae.

In some embodiments, the means to supply water to the aquatic reservoir is arranged to recycle the water drained from the reservoir. The drained water is gathered and re-supplied to the arthropod larvae in the aquatic reservoirs.

In some embodiments, the means to supply water to the reservoir further comprises a filter to remove waste from the drained water before being re-supplied to the reservoir. The filter may be a mechanical filter, a biological filter or a chemical filter. The filter may also be a combination of said filters. In some embodiments, where water is recycled, the water is treated, such as to mechanically remove waste, to remove harmful chemicals, to introduce nutrients and/or beneficial chemicals, and/or to aerate the water prior to reintroduction to the reservoir.

The means to supply water to the reservoir may also comprise a water tank for storage of water prior to supply to the reservoir.

Optionally, the apparatus may comprise a sensor for measuring a specific property of the water supplied to the reservoir. Properties of the water that may be monitored include, but are not limited to, pH, temperature, conductivity, oxidation-reduction potential (ORP) and concentrations of chemical compounds such as ammonium, tetracycline and/or chemical analogues, and food for the arthropods. In some embodiments, the sensors are arranged within the water tank to measure the properties of the water to be supplied to the aquatic reservoir.

In some embodiments, the apparatus further comprises a means for automating the apparatus. The means for automation may be a microcontroller with programmable input and output peripherals, with input being provided by the sensors and output to optimize the properties of water for supply to the reservoir.

The means for draining water from the reservoir, and in particular the porous barrier, may be removable from the aquatic reservoir. This would allow ease of removal and transport of the aquatic arthropods to downstream processes in a single step.

In some embodiments, the aquatic reservoir comprises a levelling valve. The levelling valve ensures a minimum level of water in the reservoir.

The aquatic reservoir may, in some embodiments, comprise an overflow valve. In some embodiments, the overflow valve is positioned, on the horizontal plane, 180° to the position where the water enters the aquatic reservoir. The valve may be equipped with a filter, such as a mesh, to prevent escape of larvae in the event of an overflow.

In a second aspect, the present disclosure provides a method of mass rearing aquatic arthropod larvae, comprising equipping an aquatic reservoir with a porous barrier, said reservoir having means to supply water thereto and means to drain water therefrom, placing aquatic arthropod larvae within said reservoir, said barrier being adapted to prevent escape of the larvae while permitting passage of water; and replacing the water in the reservoir on a continual basis while rearing the larvae.

As used herein, the term "continual" is used to indicate that water is replaced in the reservoir on more than one occasion, or on an ongoing basis, so that there may be periods wherein the water is flushed through the reservoir, followed by periods where there is no replacement, or there may be a slow flow, for example, that is continuous.

The porous barrier may be formed such as to define a volume, such as a basket, and so the following, when referring to being in the porous barrier will be understood to include such embodiments.

In some embodiments, arthropod larvae are placed in the porous barrier such that the surface area density of larvae within the drainage means is 10 per $cm^2$.

In some embodiments, replacement of the water is automated. In some embodiments, automation is by use of a microcontroller.

Optionally, the properties of the water may be adjusted to optimal conditions for rearing larvae prior to supply to the aquatic reservoir. This may be in response to input from sensors within the means for supplying water. The adjustment may be of the concentration of oxygen, temperature, pH, conductivity, oxidation-reduction potential (ORP) or in the concentration of a chemical compound in the water.

In some embodiments, when groups of larvae are reared in identical containers sharing the same water but at different surface area densities, then conditions with greater than 10 larvae per $cm^2$ are generally associated with reduced survival to pupation, with greater overcrowding leading to further reduced survival. In some embodiments, if the same system is used with an identical number of larvae in each container at the surface area density of 10 larvae per $cm^2$, but at different effective volume densities (larvae per mL) tested, the survival to pupation for each treatment is substantially the same (>90%). In other words, surface area density (larvae per $cm^2$) is a limiting factor in the survival of the larvae to pupation independently of effective volume densities (larvae per mL).

When this value of 10 larvae per $cm^2$ or greater is applied to static water rearing tray systems currently available in the art, the resulting survival is significantly affected, with typical survival rates being less than 50%. Thus surface area density limits the number of larvae that may be grown in each tray and is the main limiting factor in production capacity of mass rearing systems currently available in the art.

There are at least two reasons as to why the currently available apparatus employing the static water rearing tray systems does not support efficient survival to pupation under conditions of >10 larvae per $cm^2$. First, the amount of food added to the trays and, second, the increasing build-up of excretory products generated by the arthropod larvae.

In a static water rearing tray system, a comparatively large amount of food is delivered once or twice a day. This results in far greater potential for spoilage organisms to grow and foul the water whilst it is not being eaten. In addition, the amount of waste produced by the larvae steadily increases as they grow and this increase results in larval toxicity at key points during their ongoing development.

In contrast, the presently disclosed apparatus ensures that larval development is not affected by the issues relating to the currently available rearing systems, as discussed above, by providing an apparatus for mass rearing aquatic arthropod larvae which is able to dilute and/or ultimately remove waste compounds that are toxic to the larvae by replacing the water in the rearing trays.

In some aspects, the apparatus for mass rearing aquatic arthropod larvae of the present disclosure (also referred to as 'the apparatus' herein) comprises an aquatic reservoir, a means to supply water to the reservoir, and a means to drain water from the reservoir. The drainage means is equipped with a porous barrier adapted to prevent the larvae from exiting the reservoir therethrough while permitting the passage of water.

The aquatic reservoir includes any container capable of containing water, drainage means and the arthropod larvae. In some embodiments, the aquatic reservoir is a tray. The tray may typically be up to 1.2 m$^2$, although the size is only limited by the ease of handling. In this regard, it is particularly preferable that the tray is a shallow tray. The tray may be made of any suitable material for containing water, drainage means and arthropod larvae, such as plastic or metal. The tray may further comprise a levelling valve to ensure that there is always a minimum level of water in the tray. Levelling valves of this type are well known in the art. For ease of reference, the aquatic reservoir or container is also referred to as a tray herein, although it will be understood that the aquatic reservoir or container is not limited thereby.

The drainage means is equipped with a porous barrier for allowing the water to be drained from the tray whilst, retaining the arthropod larvae. The water may be drained through an outlet in the tray. In some embodiments, the outlet is a valve, such as an overflow valve. The outlet may be positioned at any practical position on the tray, for example, the outlet can be orientated 180° on the horizontal plane to the position where the water is supplied to the tray. By placing the water entry and exit positions on the opposite ends of the tray, it is possible to create a horizontal flow of water across a tray.

The porous barrier can comprise any material capable of retaining the arthropod larvae whilst allowing water to freely pass therethrough and, as such, any material capable of functioning as a sieve. In some embodiments, the porous barrier is a sheet of muslin, nylon, or flexible plastic. In some embodiments, the porous barrier is made of metal, for example a metal gauze. In some embodiments, the porous barrier comprises a mesh, membrane, screen, paper, woven cloth, non-woven cloth, fabric, fiber, foam, sieve, entangled wires, electrospun polymeric fiber, or a combination thereof. In some embodiments, the porous barrier functions as an ultrafine sieve. For example, the ultrafine sieve may have a gauge of 100 µm to 200 µm. In some embodiments, the ultrafine sieve may have a gauge of 130 µm to 170 µm. The size of the gauge of the porous barrier is an important component of the drainage means, as it determines the particle size of the artificial diet that can be used in order that the food may pass through the porous barrier to the arthropod larvae retained therein.

In particular embodiments, the porous barrier has an average wire diameter. For example, a mesh, woven fabric, or entangled wires can have wires or fibers in the non-aperture portion of the porous barrier. In some embodiments, the average wire diameter ranges from about 1 µm to about 1.0 mm. In particular embodiments, the average wire diameter of the porous barrier is about 52 µm.

In particular embodiments, the average diameter of the apertures or pores of the porous barrier ranges from about 1 µm to about 2.0 mm, or from about 100 µm to 1.0 mm. In some embodiments, the average diameter of the apertures or pores of the porous barrier is between about 1 µm and about 10 µm, between about 10 µm and about 50 µm, between about 50 µm and about 100 µm, between about 100 µm and about 150 µm, between about 150 µm and about 200 µm, between about 200 µm and about 250 µm, between about 250 µm and about 300 µm, between about 300 µm and about 350 µm, between about 350 µm and about 400 µm, between about 400 µm and about 450 µm, between about 450 µm and about 500 µm, between about 500 µm and about 550 µm, between about 550 µm and about 600 µm, between about 600 µm and about 650 µm, between about 650 µm and about 700 µm, between about 700 µm and about 750 µm, between about 750 µm and about 800 µm, between about 800 µm and about 850 µm, between about 850 µm and about 900 µm, between about 900 µm and about 950 µm, between about 950 µm and about 1.0 mm, between about 1.0 mm and about 1.1 mm, between about 1.1 mm and about 1.2 mm, between about 1.2 mm and about 1.3 mm, between about 1.3 mm and about 1.4 mm, between about 1.4 mm and about 1.5 mm, between about 1.5 mm and about 1.6 mm, between about 1.6 mm and about 1.7 mm, between about 1.7 mm and about 1.8 mm, between about 1.8 mm and about 1.9 mm, between about 1.9 mm and about 2.0 mm, or more than about 2.0 mm. In particular embodiments, the average diameter of the apertures or pores of the porous barrier is between about 100 µm and about 500 µm, for example, for mosquito species, or between about 123 µm and about 152 µm, for example, for *Aedes* species.

In some embodiments, #145 to #130 meshes (aperture 123 µm and 152 µm, respectively) are used. The egg sizes of many mosquito species are available in the literature and readily found by those skilled in the art. Mosquito egg size of multiple mosquito species across several genera are shown in Table 1. Size range for egg width of each species falls within the range of 123 µm (mesh #145) to 497 µm (mesh #34). The presently disclosed apparatus and method can be used for mass production of any of the insect species listed in Table 1. Larvae sizes of *A. aegypti* range from about 1.97 to about 7.33 mm (length), with thoracic width at L2 stage between about 0.57 and about 1.47 mm. The larvae are covered in bristles which add some resistance to passing through the mesh in the sieve. A porous barrier such as a sieve with suitable aperture for each insect species can be selected, at least in part, based on the size of the eggs or larvae.

TABLE 1

Egg Size of Mosquito Species

| Species | Length (µm) | Width (µm) | Mesh# | Aperture (cm) |
|---|---|---|---|---|
| Anopheles fluviatilis | 371.5 | 141 | 145 | 0.123 |
| Culex quinquefasciatus b | 659.73 | 155.37 | 130 | 0.152 |
| Culex quinquefasciatus d | 611 | 159 | 130 | 0.152 |
| Anopheles strodei | 457.7 | 160.6 | 130 | 0.152 |
| Anopheles pseudopuncti | 555.8 | 164.3 | 130 | 0.152 |
| Culex quinquefasciatus c | 619.4 | 169.5 | 130 | 0.152 |
| Aedes aegypti | 664 | 170 | 130 | 0.152 |
| Anopheles shannoni | 471.8 | 177.7 | 130 | 0.152 |
| Anopheles apicimaculata | 556.2 | 178.6 | 130 | 0.152 |
| Aedes rubrithorax | 682.3 | 179.6 | 130 | 0.152 |

TABLE 1-continued

Egg Size of Mosquito Species

| Species | Length (μm) | Width (μm) | Mesh# | Aperture (cm) |
|---|---|---|---|---|
| Anopheles argyritarsis | 528.7 | 181.4 | 130 | 0.152 |
| Anopheles neomaculipal | 593.6 | 182 | 130 | 0.152 |
| Anopheles fluminensis | 530.8 | 187.7 | 130 | 0.152 |
| Aedes alboannulatus | 700.5 | 187.8 | 130 | 0.152 |
| Anopheles punctimaculata | 525.3 | 189.4 | 130 | 0.152 |
| Anopheles anomolophyllus | 461.7 | 190.8 | 130 | 0.152 |
| Anopheles vestitipennis | 570.7 | 193.6 | 130 | 0.152 |
| Culex quinquefasciatus a | 590.5 | 194.5 | 130 | 0.152 |
| Anopheles albimanus | 487.9 | 196.6 | 130 | 0.152 |
| Toxorhynchites brevipalpie a | 476 | 311 | 84 | 0.239 |
| Toxorhynchites brevipalpie c | 563 | 349 | 84 | 0.239 |
| Toxorhynchites brevipalpie b | 604 | 361 | 84 | 0.239 |
| Toxorhynchites splendens | 700 | 400 | 84 | 0.239 |
| Toxorhynchites ambionensis | 566 | 444 | 40 | 0.410 |
| Toxorhynchites rutilus | 783 | 531 | 34 | 0.497 |
| Toxorhynchites moctezuma | 777 | 548 | 34 | 0.497 |

The porous barrier is designed such that the arthropod larvae are retained by the porous barrier throughout their development. This may be possible, for example, by folding the sheet of muslin on itself to retain the larvae between the sheets and ensuring that the loose edges are secured. Alternatively, the porous barrier may be secured along the side walls of the tray such that it is arranged to provide a covering over the internal space of the tray. In this arrangement, the larvae are retained within the compartment formed by the tray and the porous barrier. Further alternatively, the porous barrier may be formed such as to define a volume, such as a basket. For example, the sieve-like walls of the compartment may be made of metal gauze or any other material capable of functioning as a sieve, as described above, such that the larvae are contained within the compartment. For ease of reference, the porous barrier is also referred to as a sieve herein, although it will be understood that the porous barrier is not limited thereby.

In some embodiments, the sieve is arranged to fit closely within the tray to maximize the surface area density available to the arthropod larvae retained within the sieve. In some embodiments, the sieve is arranged to be removable from the container. This facilitates easy transfer of larvae/pupae retained therein to subsequent downstream processes in a single step.

The trays and associated sieves may be arranged one on top of another to provide a stack. A stack may typically comprise 1 to 15 trays depending on the requirement for accessibility to the trays. For example, for a process that requires daily collection and sorting of larvae from the sieve, the stack can comprise a gap between the trays that is sufficiently large to allow direct access to the sieve therein. As a result, the number of trays in each stack will be reduced. In contrast, a process that does not require access to the sieves until a point when the apparatus is disassembled and all the larvae are harvested together would not require large gaps between the trays and therefore a single stack may accommodate more trays to increase rearing capacity. A single apparatus may contain one or more stack(s).

Any water system capable of supplying water to the trays can be used to supply water to the aquatic reservoir. Supplying water to the aquatic reservoir is also referred to as the water system herein, although it will be understood that the water system is not limited thereby. The water being supplied to the trays may come directly from the water supply. In some embodiments, the water being supplied to the trays may come from a water tank forming part of the water system. Water tanks for storing water are well known in the art. The water in the water tank may be refilled using water from the water supply. In some aspects, the water system comprises a pump for moving the water around the apparatus. Suitable pumps are well known in the art.

In some embodiments, the water system is arranged as a continuous system to recycle the water drained from the trays. In some embodiments, a recyclable water system comprises a filter to process and/or remove waste in the water collected from the trays before it is re-used. The filter may be a mechanical filter that traps physical waste in the water, for example, unconsumed food and associated spoilage organisms, arthropod waste, and other debris. The filter may be a biological filter such as a layer of microorganisms to capture and biologically degrade process pollutants. For example, a biological filter may convert harmful ammonia into relatively harmless nitrates by way of the nitrogen cycle. The filter may be a chemical filter that treats the water, for example, through processes of ion exchange, adsorption, chemical bonding and molecular destruction. Mechanical, biological and chemicals filters are well known in the art and as such will not be discussed in detail here. The water system may comprise a single filter or a combination of filters.

The water system may optionally comprise non-return valves designed to cut off water flow to a particular section of the water system. A non-return valve may be used to convert a continuous, recyclable water system to a non-recyclable water system. In a non-recyclable water system, the waste water drained from the trays is removed from the water system and clean water is supplied to the trays from either the water supply or the water tank.

The term "clean water" as used herein, within a non-recyclable water system, refers to water that has not previously been exposed to aquatic arthropod larvae. Within a recyclable water system, "clean water" may refer to water that has not been exposed to aquatic arthropod larvae, or water that has been exposed to aquatic arthropod larvae but subsequently treated and processed by filtration.

The term "waste water" as used herein, within a non-recyclable water system, refers to water that has been exposed to aquatic arthropod larvae. Within a recyclable water system, "waste water" as used herein refers to water that has been exposed to aquatic arthropod larvae but not yet subsequently treated and processed by filtration.

The water system may additionally comprise one or more sensors to monitor the properties of the water in the system. Sensors for converting measurements of a physical quantity into a signal which can be detected by an observer or by an electronic instrument are well known in the art. In some aspects, the sensors are located in the water tank to accurately monitor the properties of the water prior to supply to the trays. In other embodiments, the sensors may also be arranged at any suitable place along the water system. Any deviation from an optimal parameter for a specific property of the water in the water tank, or elsewhere in the water system, may be monitored and corrected such that the water supplied to the trays provides optimal conditions for development of the aquatic arthropod larvae. Properties of the water that may be monitored include, but are not limited to, pH, temperature, conductivity, ORP, food for the arthropods and concentrations of chemical compounds such as ammonium, tetracycline and/or chemical analogues. The sensors may also detect an upper and a lower optimal water level as predetermined, within the water tank. Optionally, the water in the water tank may be removed and the water tank re-filled with water from the water supply, via a drain and flood process, and the properties of the water restored to optimal conditions prior to supply to the trays.

The apparatus may additionally comprise a suitable means for automating the apparatus, and in particular the water system. In some embodiments, the means for automation is a microcontroller. A microcontroller is a small computer on a single integrated circuit containing a processor core, memory and programmable input/output peripherals. Such microcontrollers are well known in the art and will not be described further here.

Programmable output peripherals controlled by the microcontroller may provide automated control over processes for maintaining the water in the water tank at an optimal condition and at a suitable level. In this regard, the output peripherals may provide programmable control of the addition of, for example, tetracycline and/or chemical analogues, and food. Output peripherals may also provide programmable control of the temperature, conductivity, ORP and pH of the water supply, as well as programmable control of the draining of the existing water in the water tank and subsequent replenishment with water from the mains. Alternatively, if draining of the water in the water tank is not required, the output peripherals may provide automated control of topping up of the water from the water supply to maintain a minimum level of water in the water tank. The programmable output peripherals may be controlled by the microcontroller in response to signals from programmable input peripherals, such as sensors. Sensors suitable for providing input to the microcontroller are discussed above.

Each tray and associated sieve within a stack is bathed in a flow of water supplied by the water system. The water may be supplied to each tray by a cascade of flowing water. Alternatively, the water system may be arranged to provide a direct, separate supply of water to each tray. The cascade approach relies on an alternating drain system where water from the tray above enters the tray below and then drains from an overflow valve that is orientated 180° from the original drain point. This ensures a movement of water across the tray beneath. Temperature comparisons within the system have demonstrated steady state when the flow rate is sufficient.

The supply of water to each tray may be continuous. Alternatively, the water may be supplied to the trays at set intervals. The supply of water and, where applicable, the duration of each interval may be fixed or may be in response to an input, for example, the levelling valve in the trays. In some embodiments, the flow rate of the water supplied to the trays is controllable.

In some embodiments, the flow rate of the water supply to the apparatus is between about 0.5 L/min and about 5 L/min. In particular embodiments, the flow rate is between about 0.5 L/min and about 1.0 L/min, between about 1.0 L/min and about 1.5 L/min, between about 1.5 L/min and about 2.0 L/min, between about 2.0 L/min and about 2.5 L/min, between about 2.5 L/min and about 3.0 L/min, between about 3.0 L/min and about 3.5 L/min, between about 3.5 L/min and about 4.0 L/min, between about 4.0 L/min and about 4.5 L/min, between about 4.5 L/min and about 5.0 L/min, or more than about 5.0 L/min. In particular embodiments, the flow rate is about 3.0 L/min, which achieves a constant temperature in the trays and refreshes the water in a try within an acceptable time.

In some embodiments, water constantly enters the top of the system at a fixed flow rate. In one aspect, the drain hole size maintains a fixed flow rate to the next layer down. Thus, in some embodiments, the drain hole size of the trays at different layers can be different in order to maintain a fixed flow rate at which water is supplied to each layer. In some aspects, the rate of flow from the standpipe is the same but results in a water level in the tray that may be higher than the standpipe. In particular embodiments, the flow rate remains constant through the cascade. If this is not the case, the tray water level would increase and overflow if the entry flow is higher than the exit flow. In some embodiments, a constant depth of water in the tray and a constant flow rate at the correct speed are maintained to ensure proper larval development. Whilst there are no doubt some system losses (e.g., due to friction) within the tray/sieve combination, the mesh is sufficiently transparent to not cause any major flow rate variations. In some aspects, the sieve limits the flow near the drain hole and therefore enables larvae to avoid being killed at the drain point.

The method for mass rearing aquatic arthropod larvae using the apparatus described above, involves the steps of placing the larvae within the sieve, subsequently placing the sieve containing the larvae in the tray and replacing the water in the trays.

The number of arthropod larvae placed within the tray and associated sieve may be such that the surface area density of larvae is between 0.5 and 20 per $cm^2$, or between 1 and 12 per $cm^2$. In some embodiments, the surface area density of larvae is between 5 and 10 per $cm^2$, or between 9 and 10 per $cm^2$. In some embodiments, the surface area density of larvae is about 5.0, about 5.5, about 6.0, about 6.5, about 7.0, about 7.5, about 8.0, about 8.5, about 9.0, about 9.5, about 10.0, about 10.5, about 11.0, about 11.5, about 12.0, about 12.5, about 13.0, about 13.5, about 14.0, about 14.5, or about 15.0 per $cm^2$. The surface area in the aquaculture system is a parameter for achieving an optimum pupal recovery (% survival) when rearing at high densities. In some embodiments, the density of larvae in a tray is about 10 larvae per $cm^2$ for mass rearing purposes to achieve >70% survival. In some embodiments, trays contain sufficient water, which is dependent on the height of the standpipe, that results in a larvae density of between about 1,000 and about 5,000 larvae per liter of water, or between about 1,500 and about 4,000 larvae per liter. In some embodiments, the larvae density in a tray is between about 1,500 and about 2,000, between 2,000 and about 2,500, between about 2,500 and about 3,000, between 3,000 and about 3,500, between about 3,500 and about 4,000, or more than about 4,000 larvae per liter of water. In some aspects, the density in the overall system including reservoir does not exceed 3,000 larvae per liter.

In some embodiments, the step of supplying water to the trays and associated sieves to replace the existing water therein is under automated control. Automation may be through a microcontroller as previously described.

Optionally, the properties of the water may be adjusted prior to supply to the trays to provide optimal conditions for development of the aquatic arthropod larvae. Examples of specific properties of the water that may be adjusted have been discussed previously. The adjustment may be manual or it may be under automated control in response to sensors in the water system as previously described. The adjustment to the properties of the water may be to the water in the water tank or water at any other suitable point in the water system.

Therefore, the present invention provides an apparatus and methods for mass rearing aquatic arthropod larvae that provides an accurate and constant supply of nutrient and, where necessary, antibiotics under automated control to ensure that conditions for development of the larvae is optimum, whilst the water quality is monitored to control for pH, conductivity and potential spoilage. The water flow through the sieves is arranged such that flow through the system results in an efficient, staggered flow maintaining a fixed temperature gradient throughout the trays.

The use of optimized surface area density of larvae together with the regulation and control of the specific properties of the water supplied to the larvae permits a high survival to pupation at intensive larval densities. The additional ability of the water system to automatically drain and refill under automated control also permits optimal conditions for mass rearing of aquatic arthropod larvae.

An embodiment of the present invention will now be described with respect to the figures.

Figure 2:
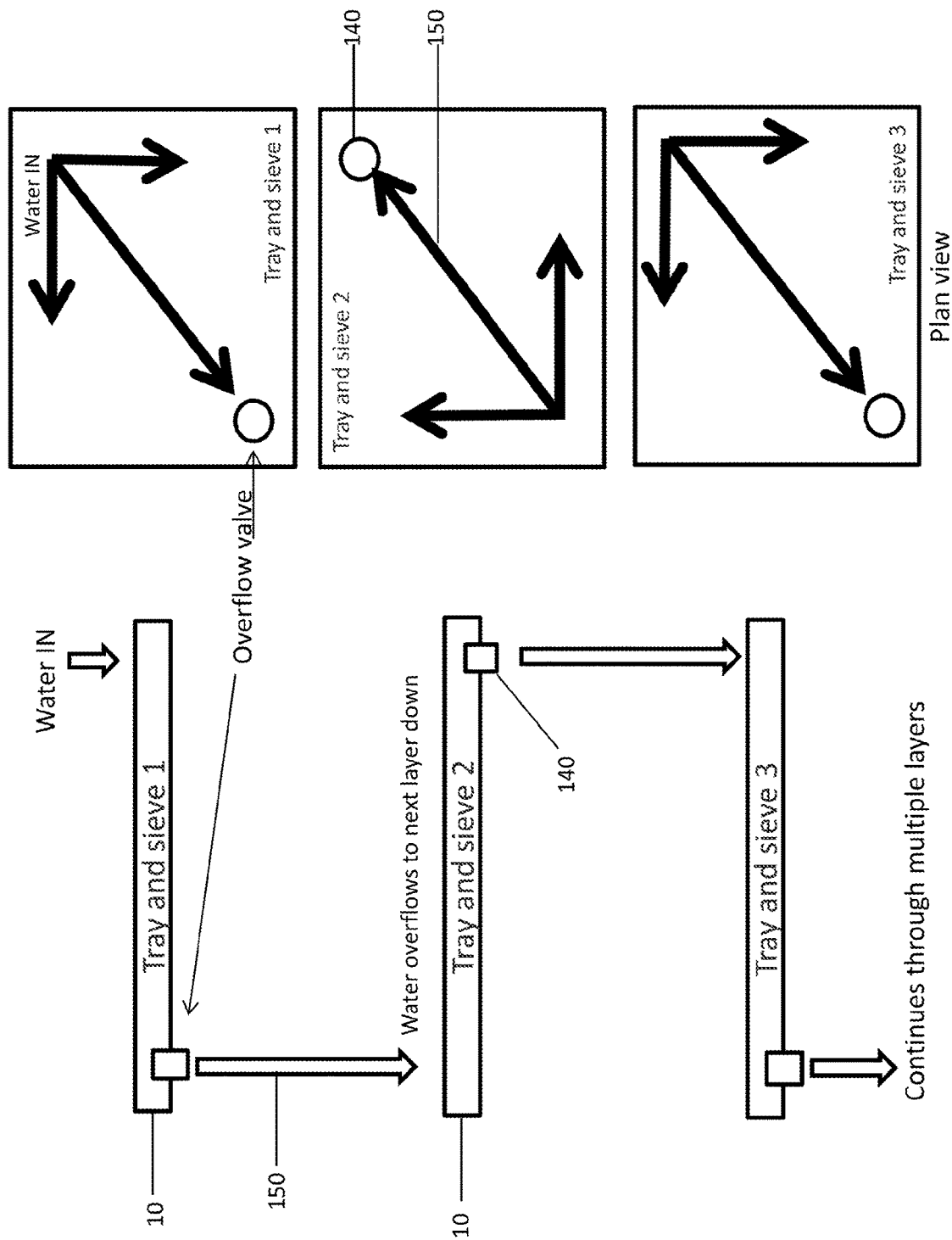
FIG. 2 shows a schematic representation of an alternating drain system for flowing water across the trays according to an embodiment of the present disclosure.

The apparatus (130) of the present invention in an embodiment as shown in FIG. 1 comprises trays and associated sieves (10) arranged one on top of another to form a stack (20). The apparatus comprises multiple stacks. The top of each stack is connected by pipes (30) to the water tank (40) such that clean water may be supplied to each tray and associated sieve (10) in the stack (20). Each tray and associated sieve is bathed in a flow of water supplied by the water system. The water may be supplied to each tray and associated sieve (10) by a cascade of flowing water employing an alternating drain system, as shown in FIG. 2, where water from the tray and sieve (10) above enters the tray and sieve below and then drains from an overflow valve (140) that is orientated 180° from the original drain point. That is to say, the overflow valve (140) is positioned at substantially the opposite end of the tray along the horizontal plane, relative to the point where the water is entering from the tray above. This arrangement ensures movement of the water (150) across the tray before being drained to the tray beneath.

In the embodiment as shown in FIG. 1, the bottom of each stack is connected by pipes (30) to a filter (50) and the filter is in turn connected by pipes to the water tank (40). As such, FIG. 1 shows a continuous water system capable of recycling the water in the apparatus. The waste water drained from the trays and associated sieves (10) is collected and passed to the filter (50) for filtration and processing. The treated water may then be returned to the water tank (40). The filter also has an outlet (60) for removing the waste water from the water system, where desired, as opposed to being transferred to the water tank (40) to be recycled.

The water tank (40) is connected via pipes to the filter (50), the water supply (80) and the stacks (20). The water tank (40) is also provided with an outlet (70) for removing the water from the water tank (40). As such, water from the apparatus may be removed from the water system from either the water tank (40) or the filter (50).

The water system is fitted with non-return valves (110) at various points along the continuous water system. FIG. 1 shows a non-return valve (110) between each of the stacks (20) and a further non-return valve between the filter (50) and the water tank (40). By closing the non-return valves (110) positioned between the stacks, it is possible to section off various modules of the apparatus. Thus, although the apparatus may have the rearing capacity of 3 or more stacks (20), its use may be limited to the desired number of stacks. Alternatively, by closing the non-return valve (110) between the filter (50) and the water tank (40), it is possible to convert the recyclable water system to a non-recyclable water system.

Both the filter (50) and the water tank (40) are each provided with two sensors (90, 100) for detecting the water level therein. The first sensor (90) detects the lowest optimal water level and the second sensor (100) detects the highest optimal water level. Supply of water to the next module in the apparatus (either the water tank or the stacks (20), respectively) or removal of water may be dependent on input to the microcontroller (120) from the water level sensors.

The apparatus (130) is provided with a microcontroller (120) for automating the apparatus (130) and in particular supplying clean water to the trays and associated sieves (10) and maintaining the properties of the water in the water tank (40) at optimal conditions for rearing arthropod larvae. To do this, the microcontroller (120) may automate the process of sensing and regulating the temperature, ORP, conductivity and pH of the water, automate the process of feeding, collect and display data and/or automate the process of refilling and draining the water in the water tank.

Figure 3:
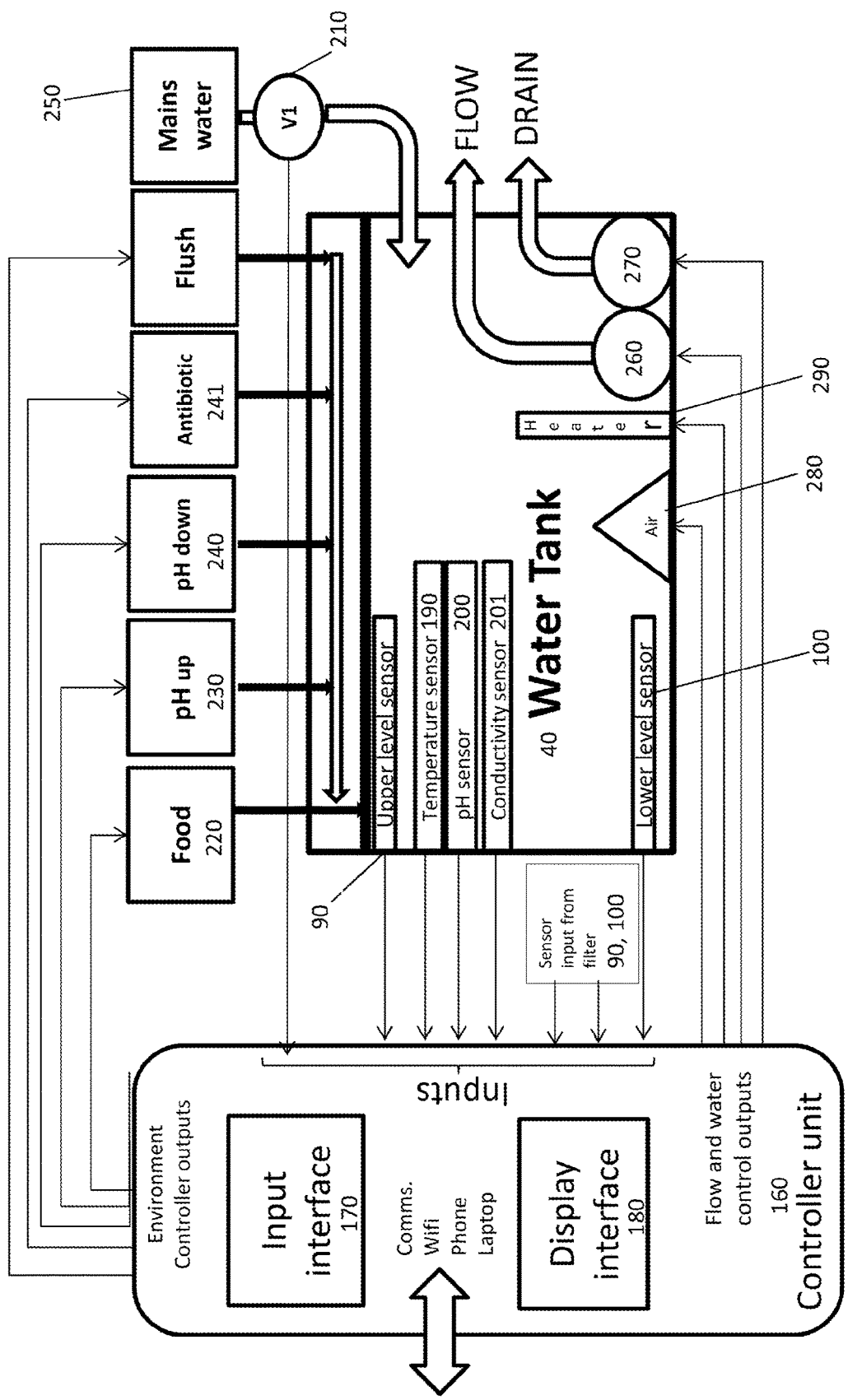
FIG. 3 shows a schematic representation of a microcontroller and associated programmable input/output peripherals used in an embodiment of the present disclosure.

A microcontroller (120) as that used in the embodiment of FIG. 1 is shown in detail in FIG. 3. The controller unit (160) comprises an input interface (170) and a display interface (180). The controller unit receives information from programmable input peripherals and regulates the properties of the water in the water and its supply to the trays and associated sieves via control of programmable output peripherals.

In the embodiment as shown in FIG. 3, the programmable input peripherals comprise sensors from both the water tank and the filter. Sensors in the water tank that detect and provide input signals to the controller unit include a temperature sensor (190), pH sensor (200), conductivity/ORP sensor (201) and sensors for detecting the optimal upper and lower water levels (100, 90 respectively). Sensors (90, 100) in the filter detect and provide input signals to the controller unit regarding the water level in the filter.

The controller unit is also connected to a sensor (210), which provides input regarding flow of water from the water supply to the water tank.

The programmable output peripherals that are controlled by the controller unit comprise an effector for adding food to the water (220), effectors for raising or lowering the pH of the water (230, 240), an effector for adding chemical compounds, for example, tetracycline and/or chemical analogues (241), and an effector for adding water from the water supply to the water tank (250). The programmable output peripherals also include effectors that regulate the flow of water into the trays from the water tank (260) and drain of water from the water tank (270) for removal from the apparatus. Further effectors regulating the properties of the water in the water tank include an effector for aeration (280), and an effector to heat the water (290).

The controller unit has the option to be connected to Wi-Fi, phone, laptop and/or other forms of network or communication device.

The claimed subject matter is described in connection with the embodiments in the detailed description, but is not limited to any particular embodiment. It is to be understood that the claimed subject matter may be embodied in various forms, and encompasses numerous alternatives, modifications and equivalents. Therefore, specific details disclosed herein are not to be interpreted as limiting, but rather as a basis for the claims and as a representative basis for teaching one skilled in the art to employ the claimed subject matter in virtually any appropriately detailed system, structure, or manner. It should be understood that the various features and functionality described in one or more of the individual embodiments are not limited in their applicability to the particular embodiment with which they are described. They instead can, be applied, alone or in some combination, to one or more of the other embodiments of the disclosure, whether or not such embodiments are described, and whether or not such features are presented as being a part of a described embodiment. For the purpose of clarity, technical material that is known in the technical fields related to the claimed subject matter has not been described in detail so that the claimed subject matter is not unnecessarily obscured.

All publications, including patent documents, scientific articles and databases, referred to in this application are incorporated by reference in their entireties for all purposes to the same extent as if each individual publication were individually incorporated by reference. Citation of the publications or documents is not intended as an admission that any of them is pertinent prior art, nor does it constitute any admission as to the contents or date of these publications or documents.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6.

As used herein, the singular forms "a", "an", and "the" include plural references unless indicated otherwise. For example, "a" container includes one or more containers.

It is understood that aspects and embodiments of the disclosure described herein include "consisting" and/or "consisting essentially of" aspects and embodiments.

Example 1

Flow Rate and Sieve Behavior

In this example, the role of the sieve and flow rate on mosquito rearing potential in a re-circulating aquaculture rearing system was assessed.

Method:

Survival of insects during mass production using a standard sieve unit (#145 Mesh, 0.123 mm aperture, 0.052 mm wire diameter, SS304 grade, woven wire mesh grade). In addition, a 13 mm I.D. pipe was formed with a piece of the same #145 SS mesh welded on to one end. The other end was left un-covered. This tube was fitted into the drain fitting and was identical to the pipes routinely used to increase the water depth in the tray system as necessary.

A digital flow meter capable of measuring flow rates between 0.5-8.0 liters per minute was installed on the water feed pipe supplying water into the top tray. Consequently, the flow rate displayed was recorded at the point of entry into the tray. Flow rate was kept constant during each of the three assessments. Three different flow rates were tested and were achieved by reducing the flow rate tap at the main pump feed pipe.

Flow rates tested were 1.0, 2.0 and 2.77 liters/min. 2.77 liters/minute was the maximum flow rate possible at the water flow outlet due to maximum pump capacity.

25,000 larvae were added each to the sieve in the top tray and the next tray down fitted with the meshed drain tube. The eggs and larvae were placed into the tray at the opposite end of the tray to the drain plug location. The larvae, eggs and water level were then observed to see if they were drawn towards the drain point.

This was repeated for each of the different flow rates. The following was observed.

Results:

TABLE 2

| Flow rate Liter/min | Time to overflow (mins) Tray with sieve tube | Time to overflow Standard sieve | Comment |
|---|---|---|---|
| 1.0 | 15:08 -> 1 hour | No overflow | No overflow Larvae not drawn rapidly to sieve tube. |
| 2.0 | 16:07-16:18 | 11 | No overflow Eggs and larvae drawn to sieve tube. |
| 2.77 | 15:56-16:01 | 5 | No overflow Eggs and larvae drawn rapidly to sieve tube. |

At the maximum flow rate possible, it took 5 minutes for the drain plug to clog resulting in water overflow from the sieve. Similarly, at a flow rate of 2.0 liters per minute, a similar overflow occurred albeit after a slightly longer time period. L1 larvae drawn to the point flow of the filtered drain pipe are unable to swim free resulting in death. Larvae from overflowed sieves upset the balance between feed and number of larvae present resulting in spoilage issues and ultimately lead to greatly reduced survival.

In this example, whilst it is possible to rear larvae in flow rates as low as 1.0 liter per minute and therefore potentially without the sieve present, the system may require a higher flow rate to ensure a constant water temperature throughout all points of the system. Temperature gradients between the farthest points of the system can be significant and as temperature is a fundamental aspect to synchronous larval mass development, the resulting rearing success is much reduced if the flow level is not at the required level. Finally, some larvae and eggs are always drawn to the filter drain point even at the slowest flow rate and so although after 1 hour the system did not over flow there was nevertheless a build-up of eggs and larvae on the mesh which potentially could cause overflow at a later time point Discussion:

In this example, using the multiple tray system described above, a flow rate of at least 3.0 liters per minute is required to ensure a complete water mix and a steady temperature across the system. Therefore, at least 3.0 liters per minute flow rate can be used to ensure correct system operation and optimum conditions required for mosquito production. At this flow rate, one would clearly encounter flow issues without the sieve included.

The density of larvae present in each tray is approximately 3,800 larvae per liter and it is this high density that makes the aquaculture system attractive as a mosquito mass production system. As a consequence however, such high densities are highly likely to create conditions by which live mosquitoes will frequently occur around the drain point due to the cascading water flow between trays and hence the probability that the insects concerned will be trapped and ultimately perish.

REFERENCES

1. Morlan, Harvey B., Hayes, Richard O., and Schoof, Herbert F. 1963. Methods for rearing *Aedes aegypti* L. Public Hlth Reept. 78:711-719.
2. Fay, R. W., McCray, J R., and Kilpatrick, J. W. 1963. Mass production of sterilized male *Aedes aegypti*. Mosquito News Vol 23, No 3. 210-214.
3. Gerberg, Eugene J., Hopkins, Thomas M., and Gentry, James W. 1969. Mass rearing of *Culex pipiens* L. Mosquito News Vol 29, No 3. 382-385.
4. Ansari, M. A., Singh, K. R. P., Brooks, G. D., Malhotra, P. R. and Vaidyanathan. V. 1977. The development of procedures and techniques for mass rearing of *Aedes aegypti*. Indian J. Med. Res. 65 (Suppl) 91-99.
5. Singh, K. R. P., Patterson, R. S., LaBrecque, G. C. and R. K. Razdan. 1972. Mass rearing of *Culex fatigans*. WHO/VBC/72.386: 26P. (7 FIG.) AND 1975. J. COMMUN. DIS. Pp 1-26.
6. Singh, K. R. P., Razdan, R. K. 1975. Mass rearing of *Culex pipiens* fatigans WIED. Under ambient conditions. WHO/VBC/75.537: 6P. (1 FIG.) (DPMIAC LOC: WHO SHELF. pp 1-6.
7. Balestrino, F., Benedict, M. Q. and Gilles, J. R. L. 2012. A New Larval Tray and Rack System for Improved Mosquito J. Med. Entomol. 49(3): pp 595-605.
8. Dame, D. A., Lofgren, C. S., Ford, H. R., Boston, M. D., Baldwin, K. F. and G. M. Jeffery. 1974. Release of chemosterilized males for the control of *Anopheles albimanus* in El Salvador. II Methods of rearing, sterilizations and distribution. Am. J. Trop. Med and Hyg. Vol 22. NO. 2. Pp 282-287.

What is claimed is:

1. An apparatus for rearing aquatic insect larvae, comprising:
   (1) a container comprising a porous barrier having an average aperture diameter ranging from about 100 μm to about 1,000 μm, which partitions the container into a first chamber and a second chamber, wherein:
   the second chamber comprises a drain outlet;
   the porous barrier prevents the insect larvae from exiting the first chamber into the second chamber while permitting at least the passage of water between the chambers, when water is supplied to the first chamber and drained from the container via the drain outlet of the second chamber; and
   the porous barrier retains the insect larvae in the first chamber for their development;
   (2) a water tank that stores water supplied to the container, wherein:
   the water tank is connected, directly or indirectly, to a pipe for supplying water to the container;
   wherein the water tank is connected, directly or indirectly, to the drain outlet of the second chamber via a filtering device whereby water drained from the container is recycled and supplied to the container; and
   wherein the filtering device comprises a waste outlet for removing waste and filters water drained from the container.

2. The apparatus of claim 1, wherein the drain outlet comprises a valve and/or a pipe sealed or affixed on the drain outlet opening.
3. The apparatus of claim 2, wherein the valve is an overflow valve, and wherein water passes from the container through the overflow valve after the maximum water level has been attained in the container.
4. The apparatus of claim 1, wherein the drain outlet is positioned substantially 180° on a horizontal plane to the position where water enters the container.
5. The apparatus of claim 1, further comprising a sensor for measuring a property of water supplied to and/or drained from the container.
6. The apparatus of claim 5, wherein the sensor measures the concentration of oxygen, temperature, pH, conductivity, oxidation-reduction potential (ORP), or concentration of a chemical compound.
7. The apparatus of claim 1, further comprising a levelling valve arranged to maintain a minimum level of water in the container, and/or a microcontroller for automating the apparatus.
8. The apparatus of claim 1, wherein the porous barrier is removable from the container, and/or permits the passage of feed, waste, and other debris, including waste produced by the insect larvae.
9. The apparatus of claim 1, wherein the porous barrier comprises a mesh, membrane, screen, paper, woven cloth, non-woven cloth, fabric, fiber, foam, sieve, entangled wires, electrospun polymeric fiber, or a combination thereof.
10. The apparatus of claim 9, wherein the porous barrier has an average wire diameter ranging from about 1 μm to about 1,000 μm.
11. The apparatus of claim 1, which is used for mass rearing of the aquatic insect larvae at a density ranging from about one larva to about 12 larvae per $cm^2$ of the bottom plate of the container, or at a density of about 10 larvae per $cm^2$ of the bottom plate of the container, and/or for rearing aquatic insect larvae at a density ranging from about 1,500 larvae to about 4,000 larvae per liter of water in the container.
12. The apparatus of claim 1, which comprises a plurality of the containers.
13. The apparatus of claim 12, wherein at least some of the plurality of containers are sequentially connected to each other or stacked on top of one another, wherein water passes from the first container in the sequence or stack through intervening container(s) to the last container in the sequence or stack, wherein the first container is connected to or supplied by a pipe supplying water and the last container is connected to a pipe draining water, and wherein the drained water is recycled to the first container, and/or
   wherein at least some of the plurality of containers are connected in parallel to the pipe supplying water and/or the pipe draining water, and wherein the drained water is recycled to the containers.
14. A method for rearing aquatic insect larvae, comprising:
   (1) placing insect larvae or eggs of an aquatic insect in the apparatus of claim 1 wherein the insect larvae or eggs are placed in the first chamber;
   (2) supplying water on a continual basis and other suitable conditions in the container for rearing the insect larvae or eggs in the first chamber, wherein the porous barrier that separates the first chamber from the second chamber of the container prevents eggs or larvae from exiting the first chamber into the second chamber while permitting at least the passage of water between the chambers, and wherein water is drained from the container via the drain outlet of the second chamber; and (3) retaining the insect larvae or eggs in the first chamber for their development.

15. The method of claim 14, wherein water is supplied to the container at a flow rate of between about 0.5 L/min and about 5 L/min, or at about 3 L/min.

16. The method of claim 14, wherein the flow rate of water draining from the container is substantially the same as the flow rate at which water is supplied to the container.

17. The method of claim 14, further comprising adjusting the flow rate at which water is supplied to the container, and/or adjusting the flow rate of water draining from the container.

18. The method of claim 14, wherein water is supplied to the container at a flow rate that maintains the temperature in the container at about 22±3° C., about 26±2° C., or between about 25° C. and 28° C.

19. The method of claim 14, wherein the aquatic insect is a mosquito of the genera *Stegomyia, Aedes, Anopheles, Culex,* or *Toxorhynchites*.

20. The method of claim 19, wherein the mosquito is *Aedes aegypti, Aedes albopictus, Culex pipiens, Culex quinquefasciatus, Anopheles stephensi, Anopheles albimanus,* or *Anopheles gambiae*.

21. The apparatus of claim 1, wherein the aquatic insect is a pest.

22. The apparatus of claim 1, wherein the aquatic insect is a mosquito of the genera *Stegomyia, Aedes, Anopheles, Culex,* or *Toxorhynchites*.

23. The apparatus of claim 22, wherein the mosquito is *Aedes aegypti, Aedes albopictus, Culex pipiens, Culex quinquefasciatus, Anopheles stephensi, Anopheles albimanus,* or *Anopheles gambiae*.

24. The apparatus of claim 1, wherein the pipe for supplying water comprises a filter.

25. The apparatus of claim 24, wherein the filter is a mechanical filter, a biological filter, a chemical filter, or a combination thereof.

26. The apparatus of claim 1, wherein the average aperture diameter of the porous barrier ranges from about 123 µm to about 152 µm.

* * * * *